United States Patent [19]
Schwartz-Feldman

[11] Patent Number: 5,501,371
[45] Date of Patent: Mar. 26, 1996

[54] MIXING SYRINGE

[76] Inventor: Jean Schwartz-Feldman, Rte. 1, Box 55, New Ulm, Minn. 56073

[21] Appl. No.: 271,796

[22] Filed: Jul. 7, 1994

[51] Int. Cl.$^6$ .............................. B01F 15/02; B67D 5/56
[52] U.S. Cl. ...................... 222/136; 222/137; 222/145.6; 366/130; 366/308
[58] Field of Search .......................... 222/129, 135–137, 222/145, 256, 386, 145.5, 145.6; 366/130, 189, 308

[56] References Cited

U.S. PATENT DOCUMENTS

| | | | |
|---|---|---|---|
| 3,140,078 | 7/1964 | Krahe et al. | 222/386 X |
| 3,144,966 | 8/1964 | Cook | 222/145 X |
| 3,164,303 | 1/1965 | Trautmann | 222/546 X |
| 3,437,242 | 4/1969 | Poitras | 222/386 X |
| 3,606,094 | 9/1971 | Mills et al. | 222/145 |
| 3,730,394 | 5/1973 | Woodson | 366/130 X |
| 4,208,133 | 6/1980 | Korte-Jungermann | 366/130 |
| 4,676,406 | 6/1987 | Frischmann et al. | 222/145 X |
| 5,192,131 | 3/1993 | Hatfield | 366/308 |
| 5,240,322 | 8/1993 | Haber et al. | 366/130 |

*Primary Examiner*—Kevin P. Shaver
*Attorney, Agent, or Firm*—Patterson & Keough

[57] ABSTRACT

This invention relates to a mixing syringe capable of storage of a plurality of compounds that provides for selectively mixing the components, the mixing portion having a first position for separating the components within the storage area, a second position for substantially mixing the components held in the storage area, and a third position providing for complete extrusion of the mixed copmpounds through an applicator tip onto the working surface.

11 Claims, 3 Drawing Sheets

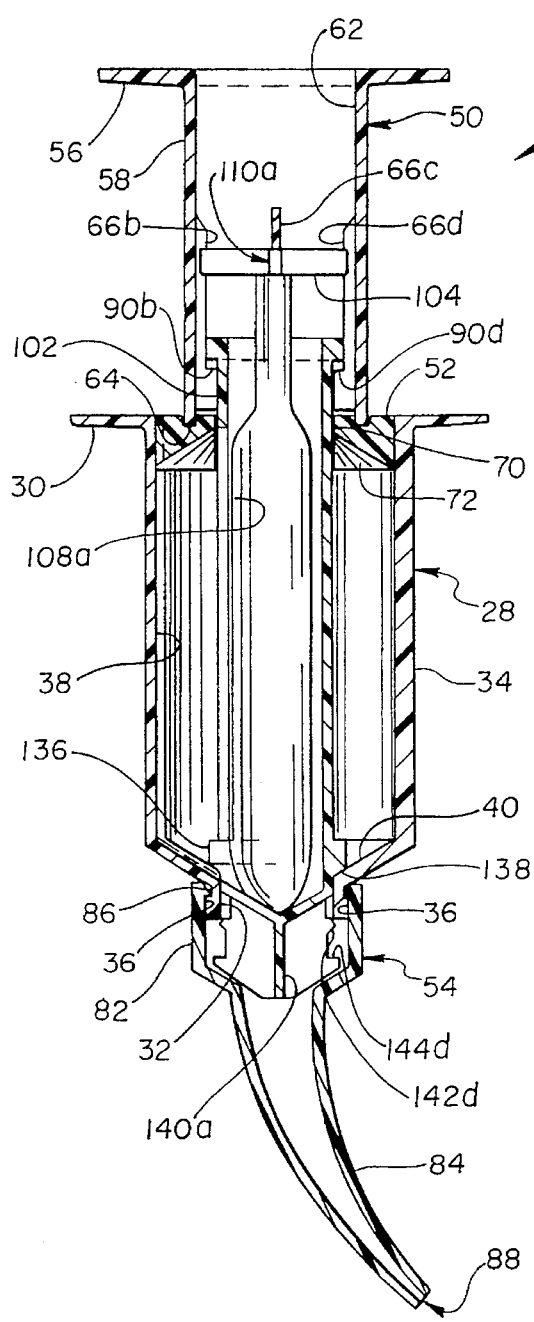
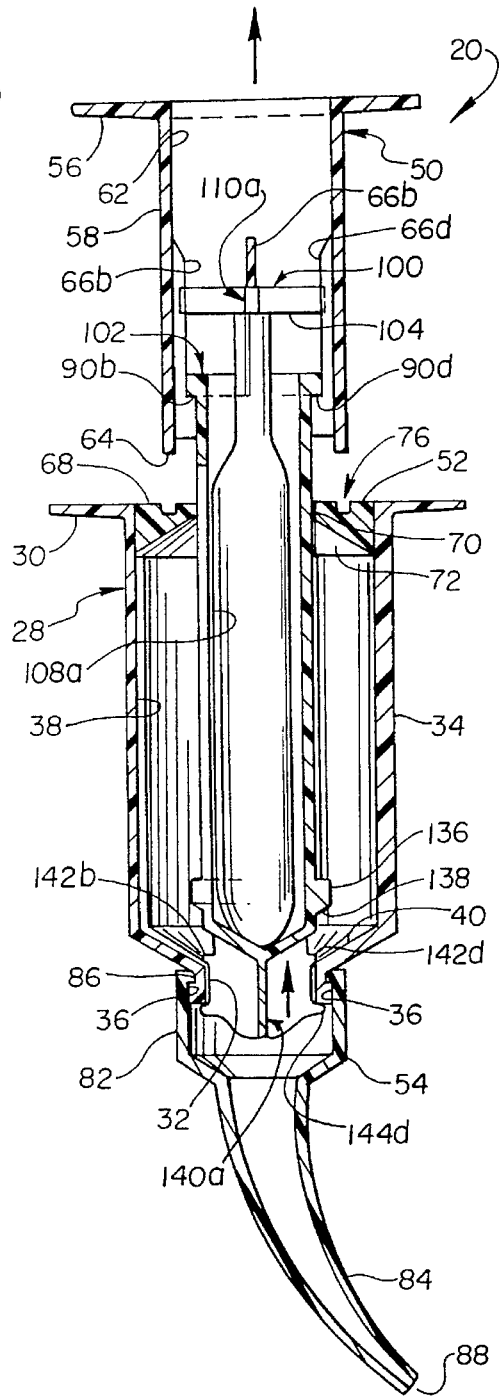
Fig. 7
Fig. 8

MIXING SYRINGE

FIELD OF THE INVENTION

This invention relates generally to a mixing syringe and in particular to a syringe for storing multiple components within the syringe, and for mixing the components prior to extrusion. The mixing syringe is particularly well adapted for use in dental procedures.

BACKGROUND OF THE INVENTION

The process of mixing a substrate with a catalyst for driving a chemical reaction to transform the substrate from a liquid to a solid is well known in the art. The various substrates and catalysts used are numerous and extremely variable in both chemistry and in application. Examples of substrates are those used in thermoplastic and thermoset reactions. In these reactions a liquid polymer is chemically and physically transformed into a solid polymer. The characteristic of a thermoplastic material is that it will melt when sufficiently heated. Thermoset materials when heated will, instead, undergo oxidative destruction before melting.

Whether the end product is thermoplastic or thermoset will depend on the chemistry of the substrate and catalyst used. The presence or absence of cross-linking from one polymeric chain to another essentially dictates whether the end product will be a thermoplastic or a thermoset. The substrate chemistry will also control whether the end product will be rigid, pliable, or elastomeric or rubbery.

The reaction converting a liquid plastic to a solid plastic is often enhanced by the addition of a catalyst. Many polymerization reactions transforming a liquid plastic to a solid plastic will occur in the absence of a catalyst, but the reaction is sufficiently slow as to be negligible in most circumstances. The addition of a catalyst substantially increases the reactive rate if not actually also contributing to the structural form of the final product. The type of catalyst is also quite variable. Catalytic activity may also involve using heat; electromagnetic radiation such as infrared, visible, or ultraviolet energy for initiating a reaction; dark reactions; as well as reactions where just adding the catalyst begins the chemical reaction which is usually exothermic in nature and is self-sustaining to completion.

The specific nature and characterization of these numerous reactions and end products is beyond the scope of this discussion. The single common characteristic inherent to all of these reactions is the essential and necessary mixing together of one component with another in order to begin the polymerization process resulting in an end product. Examples of these reactions are well known even to the general population, and are readily apparent in many household items. For instance, epoxy glues and cements are commercially available and purchased in two containers, providing for directions on mixing, usually in equal parts, the contents from the two containers, then applying the mixture to a work surface, and finally, allowing sufficient time for the epoxy glue to set. The epoxy glue compounds are stored in separate containers and the mixing procedure and application step are left to the purchaser to perform at the time of use.

Another example may be found in the field of dentistry, specifically the methods used to obtain dental impressions. Here, a substrate and catalyst are mixed together to form a paste like compound which is then impressed over the teeth, allowed to solidify, and then removed. This particular end product is chosen for its rubber like characteristics as well as its flow characteristics for obtaining dental impressions. As in all of the above noted reactions, the substrate material and catalyst are brought out of their respective storage containers, mixed together in another vessel by the dentist or dental assistant and then applied to the patient's dentition.

This mixing step can be quite cumbersome to use as well as messy and wasteful of the material. Often times the mixing step requires supplying additional mixing vessels and instruments separate from the storage containers the compounds are stored in. Just as in the epoxy glue that is commercially available in hardware stores, the two compounds are purchased and stored in separate containers, but when needed for use, appropriate amounts of the substrate and catalyst are extruded onto a surface and physically mixed by the end user prior to application. The application process additionally requires other instruments or tools by the end user to apply the mixed substrate and catalyst to the working surface in a timely fashion so as to complete the application process prior to solidification of the mixture.

The storage of the compounds, the mixing of the compounds, and the application of these compounds are carried out in three separate and distinct steps. An apparatus that provided for storage, mixing and application within a single device would provide decided advantages. The present method of providing separate storage mixing and application containers and utensils is not cost efficient and often times is wasteful of the materials.

SUMMARY OF THE INVENTION

This invention solves the problems and drawbacks in using substrates requiring catalysts for providing an end product by having a mixing syringe comprising a storage area, an extrusion means for application of the mixed end product, and a selectively separating mixing component having a first position for separating the components within the storage area, a second position for substantially mixing the components held in the storage area, and a third position providing for complete extrusion of the mixed substrate through an applicator tip onto the working surface.

BRIEF DESCRIPTION OF THE DRAWINGS

FIG. 7 is similar to FIG. 1, but with the mixing paddle in its mixing configuration;

FIG. 8 is similar to FIG. 7, but with the mixing paddle retracted, the mixing cylinder lifted, and extrusion valve opened;

DETAILED DESCRIPTION OF THE PRESENT INVENTION

Figure 1:
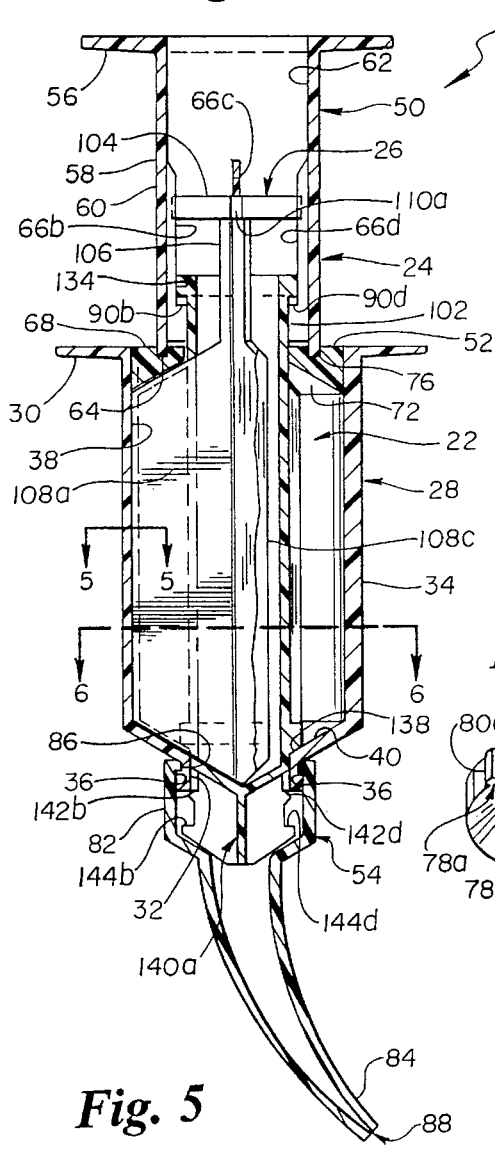
FIG. 1 is a sectional elevation view of an embodiment of the present invention.
Figure 2:
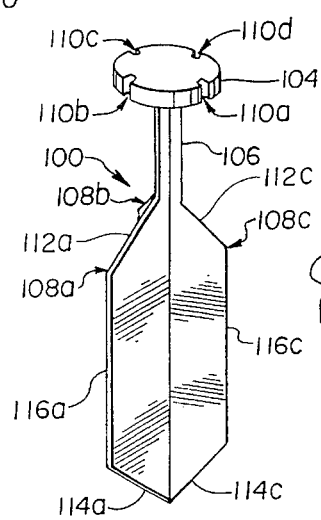
FIG. 2 is a perspective view of a paddle mixing component.
Figure 3:
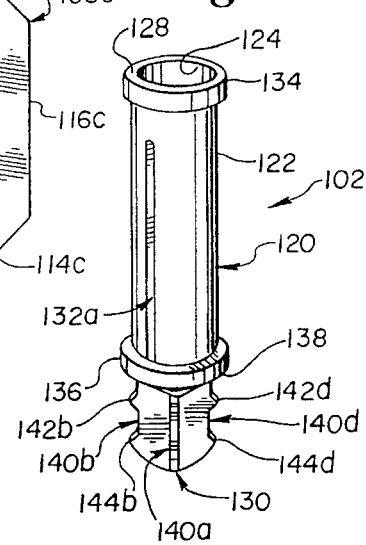
FIG. 3 is a perspective view of a paddle mixing cylinder component.
Figure 4:
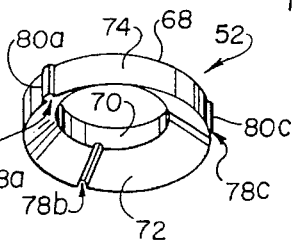
FIG. 4 is a perspective view of an annular piston component.

Referring now to the drawings, where like elements are annotated with like numerals in the various drawings, a mixing syringe 20 in accordance with the present invention comprises a storage area 22, an extrusion applicator means 24, and a mixing means 26 as depicted in FIGS. 1–6. The storage area 22 further comprises a cylindrical syringe body 28 having an annular flange 30 positioned at a proximal end of syringe body 28, a syringe throat 32 distally located on cylindrical syringe body 28, and a syringe body wall 34 interposed between annular flange 30 and syringe throat 32. Syringe throat 32 includes an annular rim 36. Syringe body wall 34 comprises an inner wall surface 38 having a bevelled surface 40 and three longitudinal grooves 42a, b, and c as more clearly depicted in FIGS. 5 and 6.

Extruder application means 24 comprises a plunger 50, an annular piston 52, and an applicator spout 54. Plunger 50 includes a proximal annular plunger flange 56, a cylindrical wall 58 having an outer surface 60, an inner surface 62, and a distal piston engaging edge 64. Inner surface 62 includes a plurality of ribs 66a, b, c, and d. Each rib 66a, b, c, and d ends in a tab step 90a, b, c, and d. Annular piston 52 comprises an upper surface 68, an inner annular surface 70, a lower bevelled surface 72, and an outer annular surface 74. Piston upper surface 68 includes an annular plunger edge groove 76. Lower bevelled surface 72 includes a plurality of paddle grooves 78a, b, and c. Outer annular surface 74 includes a plurality of raised ribs 80a, b, and c spatially located on outer surface 74 to spatially correspond to the respective paddle grooves 78a, b, and c. Raised ribs 80a, b, and c fit into grooves 42a, b, and c of syringe body wall 34.

Applicator spout 54 includes an annular collar 82 and a tapered tip 84. Annular collar 82 includes an inner raised rim 86 for mechanically engaging outer annular rim 36 of syringe body 28. Tapered tip 84 ends in opening 88.

Mixing means 26 comprises a paddle mixer 100 and a paddle mixer cylinder 102. Paddle mixer 100 includes a circular planar head 104, a stem 106, and a plurality of paddle blades 108a, b, and c. Circular planar head 104 includes a plurality of notches 110a, b, c, and d for spatially coinciding with, and mechanically engaging plunger inner ribs 66a, b, c, and d respectively. Paddle blades 108a, b, and c are radially placed around stem 106 and includes an upper bevelled surface 112a, b, and c, a lowered bevelled surface 114a, b, and c, and an outer edges 116a, b, and c. Outer edges 116a, b, and c spatially coincide with, and mechanically engage longitudinal grooves 42a, b, and c on inner wall surface 38.

Mixer cylinder 102 comprises a cylindrical body 120 having an outer surface 122 and an inner surface 124 where inner surface 124 defines paddle blade retraction area 126. Cylindrical body 120 further comprises a proximal end 128, a distal tip 130, and a plurality of paddle slots 132a, b, and c longitudinally positioned as openings through cylindrical body 120 from inner surface 124 to outer surface 122. Paddle slots 132a, b, and c are spatially arranged to coincide with and allow passage through of paddle blades 108a, b, and c respectively.

Proximal end 128 includes an annular raised rim 134 for mechanically engaging tab step 90a, b, c, and d of plunger inner ribs 66a, b, c, and d. Distal point 130 includes an annular bevelled valve surface 138 and a plurality of planar flanges 140a, b, c, and d radially positioned about the center axis of cylindrical body 120. Planar flanges 140a, b, c, and d include an upper positioning tab 142a, b, c, and d and a lower stop tab 144a, b, c, and d.

Figure 6:
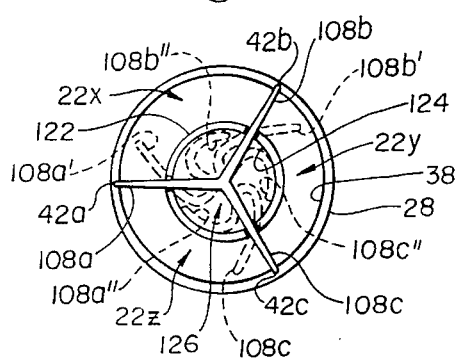
FIG. 6 is a sectional view taken at the line 6—6 in FIG. 1.
Figure 5:
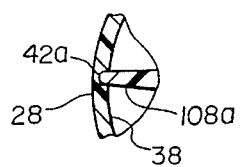
FIG. 5 is a sectional fragmentary view taken at the line 5—5 in FIG. 1.

Selective positioning of paddle blades 108a, b, and c is depicted in FIG. 6 where blades 108a, b, and c are shown in their extended positions with paddle blade outer edges 116a, b, and c engaging longitudinal grooves 42a, b, and c. In this configuration, storage area 22 is suitably compartmentalized for providing storage of three components into storage areas 22x, y, and z. An intermediate position is depicted in phantom as paddle blades 108a', b', and c' are partially retracted into paddle blade retraction area 126 through paddle slots 132a, b, and c. This intermediate position provides for mixing of the compounds stored in 22x, y, and z. The partially extended portions of paddle blades 108a, b, and c stir the components as plunger 50 is turned driving circular planar head 104 via the mechanical engagement between notches 110a, b, c, and d and plunger inner ribs 66a, b, c, and d. A fully retracted paddle blade position is depicted in phantom as paddle blades 108a", b", and c" are completely retracted into paddle blade retraction area 126 through paddle slots 132a, b, and c. In this retracted position, upper bevelled surfaces 112a, b, and c of paddle blades 108a, b, and c no longer prevent annular piston 52 from traversing storage space 22.

FIGS. 7–10 depict sequential steps in the operation of mixing syringe 20. As shown throughout the various figures, syringe 20, as depicted, is a mixing syringe with three storage compartments as shown in FIG. 6 as storage area 22x, y, and z. It is into each of these three separate compartments that, for example, a catalyst, a substrate material, and a filler material may be stored. As specifically for the case of providing a material suitable for taking dental impressions, the filler material may comprise a bulk material such as chopped fibers which serve the purpose of providing bulk to the impression-taking material, decreasing the use of expensive substrate or catalyst material. The mixing process is initiated by partially retracting paddle blades 108a, b, and c through the process of rotating plunger 50 as depicted in FIG. 7. Plunger inner ribs 66a, b, c, and d are mechanically engaged to notches 110a, b, and c, transmitting the twisting motion placed on plunger 50 to paddle mixer 100. Referring back to FIG. 6, this intermediate retracted position is depicted by the phantom line paddle blades 108a', b', and c' partially retracted into storage areas 22x, y, and z.

Continued rotation of plunger 50 results in a spinning motion of mixing means 26 about the long axis of paddle mixer 100. With the paddle blades 108a, b, and c partially retracted, the paddle blade edges 116a, b, and c are drawn through the storage areas containing the three compounds. This spinning motion provides substantial mixing action of the three separate compounds resulting in mixing together of these compounds and beginning the polymerization reaction that will ultimately result in a solid compound.

As further shown in FIG. 7, annular piston 52 is in its original starting position. Annular bevelled valve surface 138 is seated against bevelled surface 40 of the inner wall surface 38 of cylindrical syringe body 28 preventing any inadvertent leakage of the stored materials during the mixing action. Annular bevelled valve surface 138 is held firmly against bevelled surface 40 by the juxta-position of positioning tabs 142a, b, c, and d over the rim of syringe throat 32.

With the completion of thorough mixing by rotation of plunger 50 and mixing means 26, the next step is to complete the retraction of paddle blades 108a, b, and c into paddle blade retraction area 126, as previously described in reference to FIG. 6. The next step is depicted in FIG. 8 and is accomplished by pulling up on plunger 50 so that tab steps 90a, b, c, and d at the end of plunger inner ribs 66a, b, c, and

*d* engage the undersurface of annular raised rim 134. The motion pulls mixing means 26 in a direction away from applicator tip opening 88. Concurrently, this pulling motion also results in the simultaneous full retraction of paddle blades 108*a*, *b*, and *c* and unseating bevelled valve surface 138 opening storage area 22 to syringe throat 32.

Figure 9:
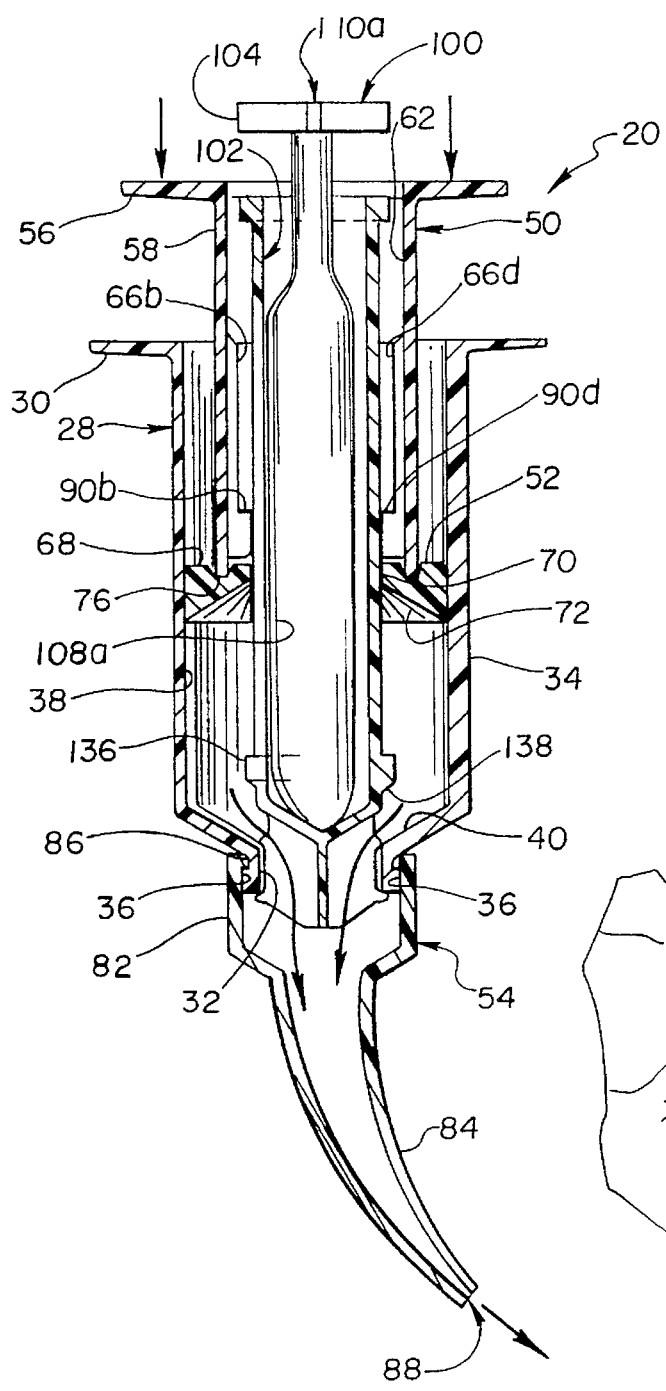
FIG. 9 is similar to FIG. 7, but with mixture partially extruded.

Extrusion of the mixed compounds is depicted in FIG. 9. Plunger 50 is pushed in the direction of the arrows driving annular piston 52 through storage area 22 and forcing the mixed components to pass through syringe throat 32 into tapered tip 84 and out tip opening 88.

Figure 10:
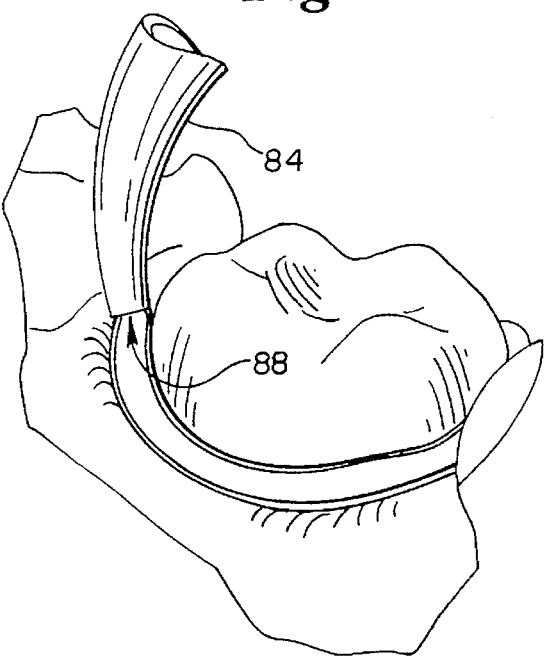
FIG. 10 is a perspective view depicting extrusion of the mixture through the applicator tip around the base of a tooth at the gingival margin.

The application of the extruded mixed components in the specific case of forming a dental impression is depicted in FIG. 10 where the mixed components are applied to the gum-dentition line as the mixed components exit tip opening 88. This invention allows for proper control of the extruded mixed components by providing the operator control over the flow rate and flow direction.

Prior art applications would require three distinct steps. The first step would involve removing the three components from their three separate storage containers and placing them onto, or into, a suitable mixing device. The second step would involve mixing the three components to begin the polymerization process. The third step would involve loading the mixed components into an appropriate apparatus in order to deliver the mixed components to the application site. All three steps are cumbersome involving tools and vessels specific for each of the three steps and require considerable time and effort on the part of the operator to perform the three steps. The present invention substantially overcomes the impediments of performing these three separate steps individually by providing a mixing syringe that combines all three steps within one self-contained device.

I claim:

1. A mixing syringe for providing a mixture from a plurality of compounds, comprising:

a storage area for selectively, separately storing a plurality of compounds;

mixing means operably carried within the storage area for substantially mixing the plurality of compounds into a mixture, where said mixing means is retractable from a storage position to a mixing position by the mixing motion such that in the mixing position the areas of separate storage become in flow communication with each other; and applicator means for selectively directionally extruding the mixture through an aperture.

2. The invention of claim 1 in which the applicator means comprises a piston and a valve operably connected to the mixing means.

3. The invention of claim 1 in which the mixing means comprises divider means for selectively positioning the mixing means between a storage position, a mixing position and an extruding position, where the applicator means can only extrude the mixture when the mixing means is in the extruding position.

4. The invention of claim 3 in which the divider means comprises flexible blades for selectively dividing the storage area into a plurality of compartments for storing the plurality of compounds such that each compound is in a compartment bordered between two adjacent flexible blades.

5. The invention of claim 4 in which the mixing means comprises first retraction means for selectively retracting the flexible blades to the mixing position such that each storage compartment communicates with each other storage compartment and the flexible blades mix the plurality of compounds into a mixture.

6. The invention of claim 5 in which the mixing means comprises second retraction means for selectively retracting the flexible blades to the extruding position such that the mixture is accessible to the applicator means.

7. A mixing syringe for providing a mixed material from a plurality of materials, the mixing material useful for molding and gluing, the mixing syringe comprising:

a hollow cylinder of a generally longitudinal shape having a broad open end and an opposed narrow open end;

mixing means operably disposed within the hollow cylinder for providing a plurality of compartments for selectively storing the plurality of materials and for selectively mixing the plurality of materials into a mixed material within the hollow cylinder, where said mixing means is retractable from a storage position to a mixing position by the mixing motion such that in the mixing position the compartments for separate storage become in flow communication with each other; and extruding means operably disposed at the broad end and narrow end of the hollow cylinder for selectively controllably extruding the mixed material out of the mixing syringe.

8. A mixing syringe for providing a mixture by mixing a plurality of materials stored in the syringe, the syringe comprising:

a main cylinder having a substantially hollow core aligned with the long axis of the main cylinder, and having an open first end and an open second end opposed to the open first end;

a spacing cylinder operably carried within the main cylinder having a substantially hollow core, an open end toward the main cylinder first end, a closed opposed end, and a plurality of longitudinal slots through the spacing cylinder wall, such that the inner surface of the main cylinder and the outer surface of the spacing cylinder define a mixing compartment open at the main cylinder first end and operably selectively closable by the spacing cylinder opposed end at the main cylinder second end;

a selectively retractable paddle mixer operably mounted within the spacing cylinder having a central longitudinal stem, a head attached at one end of the stem and a plurality of paddle blades attached edgewise along the length of the stem, each paddle blade extending out radially from the stem such that each paddle blade extends through a corresponding longitudinal slot in the spacing cylinder wall until the outer edge of each paddle blade contacts the inner surface of the main cylinder wall creating a plurality of subcompartments therein, each subcompartment containing a material useful for mixing; and an extruding cylinder operably connected to the stem and spacing cylinder, having a generally toroidally shaped piston operably connected at one end and a flange at a second opposed end such that the piston substantially fills the cross sectional area between the inner surface of the main cylinder wall and the outer surface of the spacing cylinder whereby the extruding cylinder will extrude the contents of the mixing compartment when the plurality of mixing blades have been retracted into the hollow core of the spacing cylinder, the spacing cylinder opposed end is retracted from its closable position at the main cylinder narrow end and pressure is applied to the flange.

9. A mixing syringe for providing a mixture from a plurality of compounds, comprising:

a storage area for selectively storing a plurality of compounds;

mixing means operably carried within the storage area for substantially mixing the plurality of compounds into a mixture, the mixing means comprising a divider means for selectively positioning the mixing means between a storage position, a mixing position and an extruding position, where the divider means comprises flexible blades for selectively dividing the storage area into a plurality of compartments for storing the plurality of compounds such that each compound is in a compartment bordered between two adjacent flexible blades; and applicator means for selectively directionally extruding the mixture.

10. The invention of claim 9 in which the mixing means comprises first retraction means for selectively retracting the flexible blades to the mixing position such that each storage compartment communicates with each other storage compartment and the flexible blades mix the plurality of compounds into a mixture.

11. The invention of claim 10 in which the mixing means comprises second retraction means for selectively retracting the flexible blades to the extruding position such that the mixture is accessible to the applicator means.

* * * * *